United States Patent [19]
Veerapanane et al.

[11] Patent Number: 5,874,566
[45] Date of Patent: Feb. 23, 1999

[54] IL-15 TRIPLEX OLIGONUCLEOTIDES

[75] Inventors: Dange Veerapanane, Lawrence, Kans.; Shoji Hamanaka, Kanagawa; Iwao Nozawa, Tokyo, both of Japan

[73] Assignee: Hisamitsu Pharmaceutical Co. Inc., Tosu, Japan

[21] Appl. No.: 740,215

[22] Filed: Oct. 25, 1996

[51] Int. Cl.$^6$ ............................. C07H 21/04; C12Q 1/68
[52] U.S. Cl. .................. 536/245; 536/23.1; 536/24.31; 536/24.33; 435/6; 435/91.1
[58] Field of Search .................................. 536/24.5, 23.1, 536/24.3, 24.31, 24.33; 435/375, 6, 91.1; 514/44

[56] References Cited

PUBLICATIONS

McInnes et al.; The role of interleukin–15 in T–cell migration and activation in rheumatoid arthritis; Nature Medicine, vol. 2, No. 2, Feb. 1996, pp. 175–182.

Edelbaum et al.; Interleukin (IL)–15 Promotes the Growth of Murine Epidermal Yδ T Cells by a Mechanism Involving the β– and $γ_c$–Chains of the IL–2 Receptor; J. Invest. Dermatol., 105:837–843 (1995).

Durland et la.; Binding of Triple Helix Forming Oligonucleotides to Sites in Gene Promoters; Biochemistry, 30:9246–9255 (1991).

Blauvelt et al.; Interleukin–15 mRNA is Expressed by Human Keratinocytes, Langerhans Cells, and Blood–Derived Dendritic Cells and is Downregulated by Ultraviolet B Radiation; J. Invest. Dermatol. 106:1047–1052 (1996).

Young et al.; Triple helix formation inhibits transcription elongation in vitro; Proc. Natl. Acad. Sci, 88:10023–10026 (1991).

Tu et al.; Inhibition of Gene Expression by Triple Helix Formation in Hepatoma Cells; J. Biol. Chem., 270:28402–28407 (1995).

Faucon et al.; Effect of third strand composition on triple helix formation: purine versus pyrimidine oligodeoxynucleotides; Nucleic Acids Research, 24:3181–3188 (1996).

Kovacs et al.; Triple Helix–forming Oligonucleotide Corresponding to the Polypyrimidine Sequence in the Rat α1(I) Collagen Promoter Specifically Inhibits Factor Binding and Transcpription; J. Biol. Chem; 271:1805–1812 (1996).

Rando et al.; Inhibition of T7 and T3 RNA polymerase directed transcription elongation in vitro; Nucleic Acids Research; 22:678–685 (1994).

Mori et al.; IL–15 Promotes Cytokine Production of Human T Helper Cells; J. Immunol. 156:2400–2405 (1996).

R. Stoll et al. Pharm. Res. 12(4) 465–483, 1995.

Genesis Group Assoc. Inc.—IAC Newsletter, Dialog File 636, Abs. #01997756, 1993.

Salemo et al. Immunol. 84: 404–9, 1995.

Grabstein et al. Science 264: 965–8, 1994.

Asseline et al. PNAS 81: 3297–3301, 1984.

Hanvey et al. Science 258 1481–5, 1992.

Genbank Accession # Vo3099, via STN/Genbank database, 1994.

M. Grigoriev et al J. Biol. Chem. 267(5) 3389–95, 1992.

E. Pastel et al. P.N.A.S. 88:8227–31, 1991.

F. Orson et al. Nucl. Acids Res. 19(12) 3435–41, 1991.

W. McShan et al. J. Biol. Chem. 267(8):5712–21, 1992.

L.J. Maker III et al. Bio Essays 14(12)807–815, 1992.

E. Uhlmann et al. Chem. Rev. 90(4): 543–584, 1990.

J. Milligan et al. J. Med. Chem. 36(14):1923–37, 1993.

C. Stein et al. Science 261: 1004–12, 1993.

*Primary Examiner*—John L. LeGuyader
*Attorney, Agent, or Firm*—Hovey, Williams, Timmons & Collins

[57] ABSTRACT

Oligomers for inhibiting expression of interleukin genes are described. It is believed that each oligomer, when introduced into a cell, is capable of forming a transcription-inhibiting complex composed of the oligomer and an interleukin gene. The oligomer preferably binds in the antiparallel orientation to the polypurine strand of a polypurine-polypyrimidine region of the interleukin gene.

18 Claims, 1 Drawing Sheet

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:1:

TTCCTTTCT TTCTTTTCT T 21

( 2 ) INFORMATION FOR SEQ ID NO:2:

( i ) SEQUENCE CHARACTERISTICS:
        ( A ) LENGTH: 17 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:2:

CTTTTTTCTT CTCTCTT 17

( 2 ) INFORMATION FOR SEQ ID NO:3:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

AAGGGAAAGA AAGAAAAGA A 21

( 2 ) INFORMATION FOR SEQ ID NO:4:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:4:

AAGAAAAAGA AAGAAAGGGA A 21

( 2 ) INFORMATION FOR SEQ ID NO:5:

( i ) SEQUENCE CHARACTERISTICS:
        ( A ) LENGTH: 17 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:5:

GAAAAAAGAA GAGAGAA 17

( 2 ) INFORMATION FOR SEQ ID NO:6:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

AAGAGAGAAG AAAAAAG 17

IL-15 TRIPLEX OLIGONUCLEOTIDES

BACKGROUND OF THE INVENTION

1. Field of the Invention

The present invention is broadly concerned with oligomers capable of inhibiting expression of interleukin genes, transcription-inhibiting complexes, each composed of an oligomer bound to an interleukin gene, and corresponding methods having potential as therapies for inflammatory polyarthropathy. More particularly, in preferred embodiments, each of these oligomers binds in the parallel or antiparallel orientation to the polypurine strand of a polypurine-polypyrimidine region of the transcribed region of an interleukin gene, thereby resulting in the formation of a transcription-inhibiting triplex.

2. Description of the Prior Art

Interleukin-15 is a novel cytokine having biological functions similar to those of interleukin-2 even though there is no significant sequence homology between the two. Interleukin-15 is produced by epithelial and fibroblast cell lines, and by peripheral blood monocytes. Furthermore, interleukin-15-specific mRNA has been found in several normal human tissues including placenta, skeletal muscle, and kidney (Grabstein et al., 1994, Science 264:965–968).

Interleukin-15 induces T-cell proliferation, enhances natural killer (NK) cell cytotoxicity and antibody-dependent cell-mediated cytotoxicity, and upregulates production of NK cell-derived cytokines including interferon-$\gamma$ (FIN-$\gamma$), granulocyte/macrophage-colony-stimulating factor (GM-CSF), and tumor necrosis factor-$\alpha$ (TNF-$\alpha$) (Grabstein et al., 1994, Science 264:965–968; Burton et al., 1994, Proc. Natl. Acad. Sci. 91:4935–4939; Bamford et al., 1994, Proc. Natl. Acad. Sci. 91:4940–4944; Giri et al., 1994, EMBO J. 13:2822–2830; Carson et al., 1994, J. Exp. Med. 180:1395–1403; and Giri et al., 1995, EMBO J. 14:3654–3663). Interleukin-15 also costimulates proliferation and differentiation of B cells activated with anti-immunoglobulin M (anti-lgM) (Armitage et al., 1995, J. Immunol. 154:483–490), stimulates locomotion and chemotaxis of normal T cells (Wilkinson et al., 1995, J. Exp. Med. 181:1255–1259), and promotes interleukin-5 production by T cells which may contribute to eosinophilic inflammation (Mori et al., 1996, J. Immunol. 156:2400–2405). Persistant eosinophilic inflammation in the bronchial mucosa is well recognized in the pathogenesis of chronic asthma (Bousquet et al., 1990, N. Engl. J. Med. 323:1033).

Rheumatoid arthritis is a destructive inflammatory polyarthropathy (Maini et al., 1995, in Mechanisms and Models in Rheumatoid Arthritis, pp. 25–26, eds. Henderson, Edwards, and Pettifer, Academic Press, London, 25–26). Chronic rheumatoid synovitis is characterized by the presence of activated fibroblast-like synoviocytes together with infiltration of the normally acellular synovial membrane by macrophages, T cells, and plasma cells (Duke et al., 1982, Clin. Exp. Immunol. 49:22–30). Levels of interleukin-15 in rheumatoid arthritis synovial fluid are sufficient to exert chemoattractant activity on T cells in vitro, and can induce proliferation of peripheral blood and synovial T cells; furthermore, interleukin-15 induces an inflammatory infiltrate consisting predominantly of T lymphocytes (McInnes et al., 1996, Nature Medicine 2:175–182). Therapies directed at T cells, such as cyclosporin A and monoclonal antibodies against T-cell surface antigens, produce significant clinical improvement, confirming the importance of T cells in inflammatory polyarthropathy (Horneff et al., 1991, Arth. Rheum. 34:129–140; Wendling et al., 1991, J. Rheumatol. 18:325–327; Harrison et al., 1992, in Second-line Agents in the Treatment of Rheumatic Diseases, eds. Dixon and Furst, Dekker, New York). Thus, it appears that interleukin-15 plays a significant role in T-cell recruitment and activation in inflammatory polyarthropathy.

Oligomers (i.e., oligonucleotides and oligonucleotide analogs such as protein nucleic acid) are reagents for inhibition of gene expression because of their high-affinity binding to specific nucleotide sequences. The best known strategy for causing inhibition of gene expression involves antisense oligonucleotides which bind to mRNA to inhibit its processing or translation. For example, it has been shown that the expression of the human $\alpha 1$ (I) collagen gene is effectively inhibited by antisense oligonucleotides targeted at specific regions of the $\alpha 1$ (I) mRNA (Laptev et al., 1994, Biochemis-try 33:11033–11039).

Additionally, gene promoters can serve as targets for a novel, antisense strategy, namely the triplex strategy. This strategy employs single-stranded oligomers that bind to the major groove of a polypurine-polypyrimidine region of a double-stranded DNA to form a triplex in a sequence-specific manner. These oligomers are called triplex-forming oligonucleotides (TFO's) or TFO analogs. In a polypurine-polypyrimidine region, a purine-rich DNA single strand is hydrogen bonded by Watson-Crick base-pairing to a pyrimidine-rich DNA single strand; the polypurine-polypyrimidine region is not necessarily a homopurine-homopyrimidine region in that the purine-rich DNA single strand may contain at least one pyrimidine residue and the pyrimidine-rich DNA single strand may contain at least one purine residue. These triplexes have been shown to inhibit transcriptional activity of various promoters in both in vitro and in vivo experiments (Grigoriev et al., 1992, J. Biol. Chem. 267:3389–95; Cooney et al., 1988, Science 241:456–59; Maher et al., 1989, Science 245:725–30; Ing et al., 1993, Nucleic Acids Res. 21:2789–96; Kovacs et al., 1996, J. Biol. Chem. 271:1805–1812). However, the use of oligomers to inhibit transcription of interleukin genes and to thereby suppress T-cell recruitment and activation as a method of treating inflammatory polyarthropathy is unknown in the prior art.

SUMMARY OF THE INVENTION

The present invention provides novel therapies for inflammatory polyarthopathy associated with rheumatoid arthritis and eosinophilic inflammation associated with chronic asthma. In these therapies, expression of interleukin genes is inhibited, resulting in suppression of T-cell recruitment and activation, and a concomitant alleviation of inflammatory polyarthropathy or eosinophilic inflammation.

In the present invention, a sequence-specific oligomer is introduced into a cell resulting in the production of a transcription-inhibiting complex composed of the oligomer bound to the interleukin gene. These oligomers include oligonucleotides (e.g., phosphodiester, phosphorothioate, methylphosphonate, and methylphosphonothioate oligonucleotides) and oligonucleotide analogs [e.g., protein nucleic acid, morpholino, methylene (methylimino) linkage, boronated, and pteridine oligomers]. Oligonucleotide analogs can be linked at either their 5' or 3' ends to intercalators (e.g., psoralen and acridine derivatives). Oligomers can be formulated into pharmaceutically acceptable preparations (e.g., injectable preparations, sprays, ointments, creams, gels, tablets, and perfusions).

In preferred embodiments, the oligomer is a phosphorothioate oligodeoxynucleotide having a length of at least about 5 nucleotides, preferably from about 5 to 50 nucleotides; this oligonucleotide preferably binds in the antiparallel orientation to the polypurine strand of a polypurine-polypyrimidine region of the transcribed region of the interleukin-15 gene.

DETAILED DESCRIPTION OF THE PREFERRED EMBODIMENT

Figure 1:
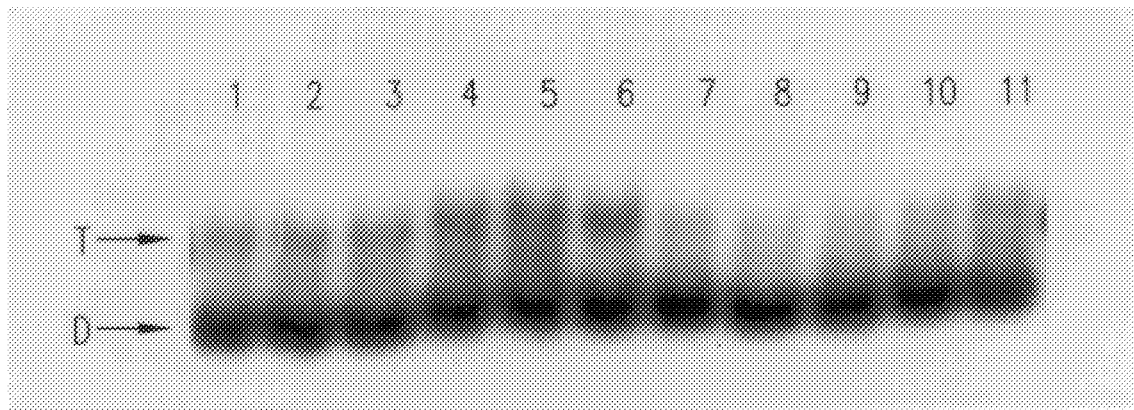
FIG. 1 is a photograph of an autoradiogram of a gel illustrating the results of a gel mobility shift analysis of oligonucleotide-directed triplex formation on a target DNA specific to the transcribed region of the interleukin-15 gene; sequence ID No. 1 was end-labeled and incubated with an excess of unlabeled Sequence ID No. 3; each reaction mixture was either incubated overnight at 22° C. and included 0.1 μg (lane 1), 0.2 μg (lane 2), 0.4 μg (lane 3), 0.8 μg (lane 4), or 1.6 μgs (lanes 5 and 6) of Sequence ID No. 3, or each reaction mixture was incubated overnight at 37° C. and included 0.1 μg (lane 7), 0.2 μg (lane 8), 0.4 μg (lane 9), 0.8 μg (lane 10), or 1.6 μgs (lane 11) of Sequence ID No. 3; D=duplex DNA and T=triplex DNA.

The following example describes preferred techniques for the synthesis of the therapeutic oligomers of the present invention, and use thereof in the inhibition of interleukin-gene expression; it is to be understood, however, that these examples are provided by way of illustration only, and nothing therein should be taken as a limitation upon the overall scope of the invention.

EXAMPLE

Materials and Methods

Oligonucleotide Synthesis and Preparation

Oligonucleotides were synthesized on an Applied Biosystems 392 DNA synthesizer. Double-stranded oligonucleotides were prepared by mixing equal amounts of complementary single strands in the presence of 0.25M NaCl. The mixture was heated to 80° C. for 5 min, incubated at 55° C. for 30 min, and then at 42° C. for 30 min. Oligonucleotides were gel purified on a 10% polyacrylamide gel, electroeluted, and precipitated with ethanol.

TABLE 1 describes the double-stranded oligonucleotides (i.e., target DNAs) of the present invention:

| Sequence ID No. of Oligonucleotide | Parent Gene | Nucleotide Position in Parent Gene |
|---|---|---|
| 1 | interleukin-15 gene | 184 to 205 |
| 2 | interleukin-15 gene | 1924 to 1940 |

TABLE 2 describes the single-stranded oligonucleotides (i.e., TFO's) of the present invention:

| Sequence ID No. of Oligonucleotide | Type | Orientation Relative to Target DNA | Sequence ID No. of Target DNA |
|---|---|---|---|
| 3 | phosphodiester | antiparallel | 1 |
| 4 | phosphodiester | parallel | 1 |
| 5 | phosphodiester | antiparallel | 2 |
| 6 | phosphodiester | parallel | 2 |

Gel Mobility Shift Analysis of Triplex Formation

Sequence ID No. 1 was end-labeled with $[\alpha^{32}P]$ATP using $T_4$ polynucleotide kinase, and was purified through a Sephadex G50 column. Approximately 30,000 cpm was incubated with 0 to 1.6 μg of Sequence ID No. 3 in a 10 μl reaction mixture including 20 mM Tris-HCl (pH 7.4), 20 mM $MgCl_2$, 2.5 mM spermidine, 10% sucrose, and 0.25 mg/ml bovine serum albumin. Incubation was conducted overnight at 22° C. or 37° C., or was conducted for 3 h at 22° C. Samples were electrophoresed through 8% polyacrylamide, 0.25% bisacrylamide gels buffered with 89 mM Tris, 89 mM boric acid (pH 7.5), and 20 mM $MgCl_2$ for 4.5 h at 10 V/cm at 6° C. Gels were then dried and autoradiographed.

Gel Mobility Shift Analyses are conducted as described above using Sequence ID No. 1 as double-stranded target DNA and Sequence ID No. 4 as single-stranded oligonucleotide, and using Sequence ID No. 2 as double-stranded target DNA and Sequence ID Nos. 5 and 6 as single-stranded oligonucleotides.

Results and Discussion

Sequence ID No. 3 Forms a Triplex with Sequence ID No. 1

The 21-bp long polypyrimidine sequence of the transcribed region of the human interleukin-15 gene occurring at nucleotide positions 184 to 205 is a rare structure; such long stretches of all C's and T's occur infrequently in other genes. It was hypothesized that a single-stranded oligonucleotide with a sequence complementary to the polypyrimidine sequence of the interleukin-15 gene would be able to form a triplex with this structure. In order to demonstrate triplex formation with this target sequence, gel mobility shift assays were performed. The detection of a triplex structure in this electrophoresis system is based on the observation that triplex DNA migrates more slowly in a polyacrylamide gel relative to duplex DNA due to the reduction of DNA charge that is likely to accompany triplex formation.

Figure 2:
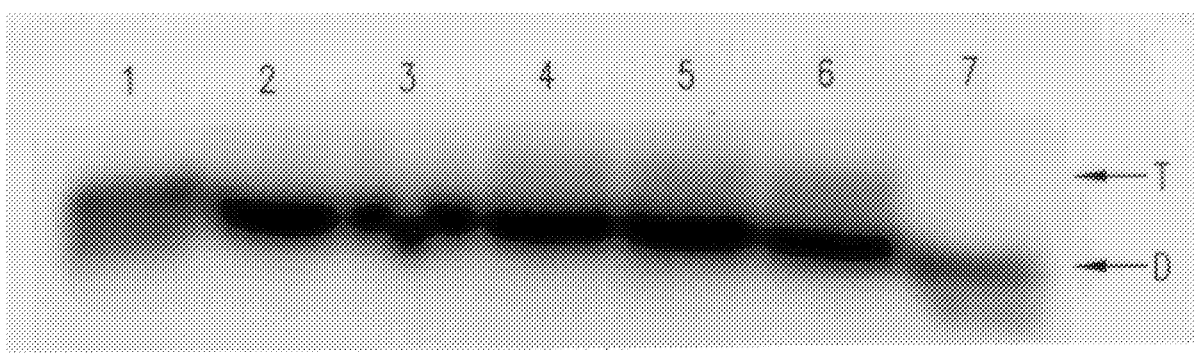
FIG. 2 is a photograph of an autoradiogram of a gel illustrating the results of a gel mobility shift analysis of oligonucleotide-directed triplex formation on a target specific to the transcribed region of the interleukin-15 gene; Sequence ID No. 1 was end-labeled and incubated with an excess of unlabeled Sequence ID No. 3; each reaction mixture was incubated for 3 h at 22° C. and included 0 μg (lanes 1 and 7), 0.05 μg (lane 2), 0.1 μg (lane 3), 0.2 μg (lane 4), 0.4 μg (lane 5), or 0.8 μg (lane 6) of Sequence ID No. 3; D=duplex DNA and T=triplex DNA.

Initial testing of triplex formation was performed using a single-stranded oligonucleotide (i.e., Sequence ID No. 3) having a sequence identical to the polypurine strand of the double-stranded target sequence (i.e., Sequence ID No. 1). Radiolabeled Sequence ID No. 1 was incubated with increasing amounts of Sequence ID No. 3. The results of this gel mobility shift analysis are shown in FIGS. 1 and 2. These figures demonstrate that the addition of increasing amounts of Sequence ID No. 3 relative to Sequence ID No. 1 results in a gradual shift from duplex (D) to a distinct slower-migrating band (T), indicating the formation of triplex DNA. Such triplex formation within the transcribed region of the interleukin-15 gene shows that oligonucleotide-directed triplex formation has utility in inhibiting elongation of primary transcripts in addition to inhibiting initiation of the synthesis of these transcripts.

We claim:

1. An oligonucleotide having a length of from about 5–50 nucleotides and which binds in a cell-free reaction mixture to the polypurine-polypyrimidine region of the transcribed region of double-stranded human IL-15 gene to form a triplex.

2. A triplex comprising the transcribed region of double-stranded human IL-15 gene having a polypurine-polypyrimidine region, and an oligonucleotide having from about 5–50 nucleotides.

3. The oligonucleotide of claim 1, wherein the oligonucleotide is DNA.

4. The oligonucleotide of claim 1, wherein the oligonucleotide is selected from the group consisting of phosphodiester, phosphorothioate, methylphosphonate, and methylphosphonothioate oligonucleotides.

5. The oligonucleotide of claim 4, wherein the oligonucleotide is a phosphodiester oligonucleotide.

6. The oligonucleotide of claim 1, wherein the polypurine-polypyrimidine region comprises a sequence selected from the group consisting of Sequence ID Nos. 1 and 2.

7. The oligonucleotide of claim 6, wherein the oligonucleotide comprises a sequence selected from the group consisting of Sequence ID Nos. 3 through 6.

8. The oligonucleotide of claim 1, wherein the oligonucleotide is capable of binding to the polypurine strand of the polypurine-poly-pyrimidine region.

9. The oligonucleotide of claim 8, wherein the oligonucleotide is capable of binding to the polypurine strand in a parallel orientation.

10. The oligonucleotide of claim 8, wherein the oligonucleotide is capable of binding to the polypurine strand in an antiparallel orientation.

11. The triplex of claim 2, wherein the oligonucleotide is DNA.

12. The triplex of claim 2, wherein the oligonucleotide is selected from the group consisting of phosphodiester, phosphorothioate, methylphosphonate, and methylphosphonothioate oligonucleotides.

13. The triplex of claims 12, wherein the oligonucleotide is a phosphodiester oligonucleotide.

14. The complex of claim 2, wherein the polypurine-polypyrimidine region comprises a sequence selected from the group consisting of Sequence ID Nos. 1 and 2.

15. The complex of claim 14, wherein the oligonucleotide comprises a sequence selected from the group consisting of Sequence ID Nos. 3 through 6.

16. The complex of claim 2, wherein the oligonucleotide is capable of binding to the polypurine strand of the polypurine-polypyrimidine region.

17. The complex of claim 16, wherein the oligonucleotide is capable of binding to the polypurine strand in a parallel orientation.

18. The complex of claim 16, wherein the oligonucleotide is capable of binding to the polypurine strand in an antiparallel orientation.

* * * * *